(12) United States Patent
Krall et al.

(10) Patent No.: US 7,020,529 B2
(45) Date of Patent: Mar. 28, 2006

(54) DEFIBRILLATION ELECTRODE COVER

(75) Inventors: Robert C. Krall, Flagstaff, AZ (US);
Louis J. Smith, Flagstaff, AZ (US);
Peter J. Zeller, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 314 days.

(21) Appl. No.: 09/848,121

(22) Filed: May 2, 2001

(65) Prior Publication Data

US 2003/0023294 A1 Jan. 30, 2003

(51) Int. Cl.
*A61N 1/05* (2006.01)
(52) U.S. Cl. ...................................... 607/122
(58) Field of Classification Search ............... 607/2, 607/5, 119, 121, 122, 153
See application file for complete search history.

(56) References Cited

U.S. PATENT DOCUMENTS

| | | |
|---|---|---|
| 2,985,172 A | 5/1961 | Jones |
| 4,011,861 A | 3/1977 | Enger |

(Continued)

OTHER PUBLICATIONS

Bardy GH et al. Some Factors Affecting Bubble Formation With Catheter-Mediated Defibrillator Pulses. Circulation 1986; 73(3):525-538.

(Continued)

*Primary Examiner*—Kennedy Schaetzle
(74) *Attorney, Agent, or Firm*—Wayne D. House

(57) ABSTRACT

An implantable electrode provided with a thin, porous, wettable polymeric covering. The electrode covering of the present invention tightly conforms to the external profile of an electrode, which minimizes air gaps and voids. The electrode covering is relatively thin, preferably less than 0.13 mm thick, and is treated to enhance rapid wetting by bodily fluids. The combination of minimal air gaps, tight conformance to the electrode, wettability and porosity of the thin covering, allows repeated, high energy electrical discharges to be transmitted without significant bubble formation, sparking or degradation of the covering. In addition, the electrode covering of the present invention has pore sizes tailored to minimize cellular ingrowth and tissue attachment thereby allowing a less traumatic removal of the electrode after implantation if extraction becomes necessary, for example due to infection or electrode dislodgment.

47 Claims, 11 Drawing Sheets

U.S. PATENT DOCUMENTS

| | | | |
|---|---|---|---|
| 4,281,669 A | | 8/1981 | MacGregor |
| 4,542,752 A | | 9/1985 | DeHaan et al. |
| 4,573,480 A | | 3/1986 | Hirschberg |
| 4,972,846 A | | 11/1990 | Owens et al. |
| 5,090,422 A | | 2/1992 | Dahl et al. |
| 5,269,810 A | | 12/1993 | Hull et al. |
| 5,358,516 A | | 10/1994 | Myers et al. |
| 5,466,252 A | | 11/1995 | Soukup et al. |
| 5,609,622 A | | 3/1997 | Soukup et al. |
| 5,755,762 A | | 5/1998 | Bush |
| 5,807,306 A | * | 9/1998 | Shapland et al. .............. 604/21 |
| 5,824,030 A | | 10/1998 | Yang et al. ................. 607/122 |
| 5,902,329 A | * | 5/1999 | Hoffmann et al. .......... 607/121 |
| 5,931,862 A | | 8/1999 | Carson ....................... 607/120 |
| 6,546,292 B1 | * | 4/2003 | Steinhaus et al. ........... 607/116 |
| 2002/0147486 A1 | * | 10/2002 | Soukup et al. .............. 607/122 |
| 2005/0164283 A1 | * | 7/2005 | Krotz et al. ................... 435/6 |

OTHER PUBLICATIONS

Cameron J et al. Stiffness Of The Distal Tip Of Bipolar Pacing Leads. PACE 1990; 13:1915-1920.

Epstein AE et al. Gross and Microscopic Pathological Changes Associated With Nonthoracotomy Implantable Defibrillator Leads. Circulation 1998; 98:1517-1524.

Fung YC. Human Red Cell Dimensions and Shape. In: *Biomechanics Mechanical Properties of Living Tissues*, New York: Springer-Verlag 1993; 112-122.

\* cited by examiner

DEFIBRILLATION ELECTRODE COVER

FIELD OF THE INVENTION

The present invention relates to the field of implantable defibrillation electrodes and more particularly to such electrodes provided with porous polymeric coverings.

BACKGROUND OF THE INVENTION

Transvenous defibrillator leads are used for the correction of ventricular tachycardia and ventricular fibrillation. Leads of this type are intravenously positioned and are used to provide a variety of sensing, pacing and defibrillation functions. More than one electrode may be provided if it is desired to provide electrodes for defibrillation as well as for pacing and/or sensing. Typical leads are positioned into the right atrium and/or the right ventricle. Recently developed leads are positioned into the coronary sinus for use with atrial defibrillation systems.

Conventional transvenous defibrillator leads use a helically wound wire to conduct the electrical energy from the connector at the proximal end of the lead to the electrode near the distal end. The conductive electrode surface is most commonly provided by leaving a portion of the helically wound wire un-insulated and exposed, allowing it to contact or be in close proximity to the desired surface of the heart. Such exposed electrodes have a fundamental disadvantage with tissue ingrowth. The ingrowth and anchoring of tissue into the exposed coil makes the lead extremely difficult to remove, if removal is required (due to, for example, infection or dislodgment).

Various electrode coverings have been suggested to eliminate or minimize the tissue attachment to the electrode. U.S. Pat. No. 5,090,422 to Dahl et al. describes defibrillation electrodes provided with coverings of porous polymeric materials including polyurethane and polytetrafluoroethylene (hereinafter PTFE). The penetration of bodily fluids permits electrical conduction through the porous polymer. Dahl et al. teach that the electrode covering is greater than 0.25 microns thick and preferably greater than 2.0 mm thick, which results in a relatively large spacing between the electrode and the tissue to be stimulated and may require a longer time duration to re-wet following the transmission of an electrical discharge. In addition, a thick electrode cover may also increase the occurrence of gas build up following the transmission of an electrical discharge. Such a gas build up increases the electrical resistance through the cover. Thick covers also increase the stiffness and profile of the electrode, which are undesirable attributes, particularly when implanted into a coronary sinus. U.S. Pat. No. 5,755,762 to Bush teaches a similar porous PTFE electrode covering.

U.S. Pat. No. 5,609,622 to Soukup et al. teaches the construction of a porous PTFE electrode cover made conductive by loading the porous covering with a conductive powdered material such as graphite. Other insulating electrode leads and conductive electrodes incorporating porous polymeric materials are disclosed in U.S. Pat. No. 4,011,861 to Enger, U.S. Pat. No. 4,573,480 to Hirschberg, U.S. Pat. No. 5,148,806 to Fukui et al., U.S. Pat. No. 5,269,810 to Hull et al., U.S. Pat. No. 5,358,516 to Myers et al. and U.S. Pat. No. 5,466,252 to Soukup et al.

A relatively thin, porous, polymeric covering, suitable for use over a coiled implantable electrode, would have numerous advantages over the previously described art. For example, thin electrode coverings are typically more flexible, reducing abrasion and irritation to surrounding tissue. A relatively thin electrode covering will typically be more conductive and positioned closer to the desired tissue. A thin electrode covering can also provide a reduced profile or outer diameter, allowing placement within smaller vessels. An improved porous electrode cover would also incorporate a material, a wetting agent, tailored to allow wetting and electrical conduction by bodily fluids. Such an improved cover would also provide a barrier to tissue ingrowth and attachment, facilitating removal if required. Furthermore, removal is desirably accomplished without requisite for surgical dissection of the tissue from the covered portion of the lead.

A typical defibrillation electrode out-gasses and forms undesirable bubbles during rapid, repeated energy pulses. Bubble formation at an electrode is described by GH Bardy et al. in "Some factors affecting bubble formation with catheter-mediated defibrillation pulses," *Circulation* 73, No. 3, 525–538, March 1986. The formation of bubbles at the electrode degrades the energy waveform. Excessive bubble formation can result in increased conduction resistance, which raises the energy required for defibrillation and increases local current density. It is desirable to provide a relatively thin electrode covering that has the additional capability of transferring repeated high-energy pulses without degrading the integrity of the covering. Thin coverings can readily diffuse bubbles through the porous covering materials during repeated defibrillation pulses.

SUMMARY OF THE INVENTION

The present invention is a thin, porous, wettable polymeric covering for an implantable electrode. The covering of the present invention tightly conforms to the external profile of an electrode, which minimizes air gaps and voids. The electrode covering is relatively thin, preferably less than 0.13 mm thick, and is treated to enhance rapid wetting by bodily fluids. The combination of minimal air gaps, tight conformance to the electrode, wettability and porosity of the thin covering, allows repeated, high energy electrical discharges to be transmitted without significant bubble formation, sparking or degradation of the covering. In addition, the electrode covering of the present invention has pore sizes tailored to minimize cellular ingrowth and tissue attachment thereby allowing a less traumatic removal of the electrode after implantation if extraction becomes necessary, for example due to infection or electrode dislodgment.

The porous character of the thin electrode covering of the present invention results in an electrode that is non-conductive in a dry state prior to implantation. When "wetted" by body fluids following implantation, the porosity of the cover results in effective delivery of a defibrillation electrical charge to surrounding tissue.

Porous materials, including porous polymers generally and in particular the preferred porous PTFE used for the electrode cover of the present invention, contain void spaces with the result that these materials have bulk densities (i.e., mass divided by gross or bulk volume) that are lower than their non-porous counterparts. Non-porous PTFE is generally considered to have a density of about 2.2 g/cc while porous PTFE has a bulk density of less than 2.2 g/cc.

The porosity, or void volume, of the electrode covering material is high enough and sufficiently uniformly distributed to enable the electrode covering material, which is non-conductive in the dry state, to be conductive when wetted by body liquids. The covered electrode of the present invention is thus conductive when implanted.

A preferred porous material for the covering of the electrode is porous expanded polytetrafluoroethylene (hereinafter ePTFE). This material has a microstructure of interconnected fibrils with void spaces between fibrils, and has a generally white, opaque appearance when dry that changes to a translucent appearance when wetted. Wetting may be accomplished by immersion in isopropyl alcohol for one minute in order to demonstrate the porous character of the PTFE covering; the porous character of the surface of the covering may also be evidenced by microscopy.

To create the electrode cover of the present invention, advances in PTFE film development were necessary. Thinner, higher strength, higher porosity, smaller pore size films have been created. Typically, increasing porosity (which is needed for fast wetting and re-wetting) comes at the expense of increasing pore size (which leads to increased tissue attachment). Also, decreasing thickness typically causes a decrease in matrix tensile strength (which compromises removal strength). This thin application requires specially developed materials that optimize material properties that appear to be mutually exclusive in the processing of ePTFE.

DETAILED DESCRIPTION OF THE INVENTION

The present invention is a thin, porous, wettable polymeric covering for an implantable electrode. The covering of the present invention is less than about 0.13 mm thick and tightly conforms to the external profile of a coiled electrode, which minimizes air gaps and voids. The minimal air gaps, wet-ability and porosity of the thin polymeric covering allow repeated high energy electrical discharges to be transmitted through the thin covering without dielectric breakdown or sparking. Such high energy electrical discharges are particularly beneficial in implantable cardiac defibrillation applications. The electrode covering of the present invention has pore size tailored to inhibit cellular ingrowth. The minimal cellular ingrowth minimizes tissue attachment, allowing a less traumatic removal of the electrode after implantation, if extraction becomes necessary, for example due to a chronic infection or electrode dislodgment. The minimal cellular ingrowth characteristic of the covered electrode of the present invention results in an electrode that is easily extractable.

A porous material wettable by body fluids is herein defined as a material that accepts body fluids within the void spaces of its pore structure under conditions of implantation.

Figure 1:
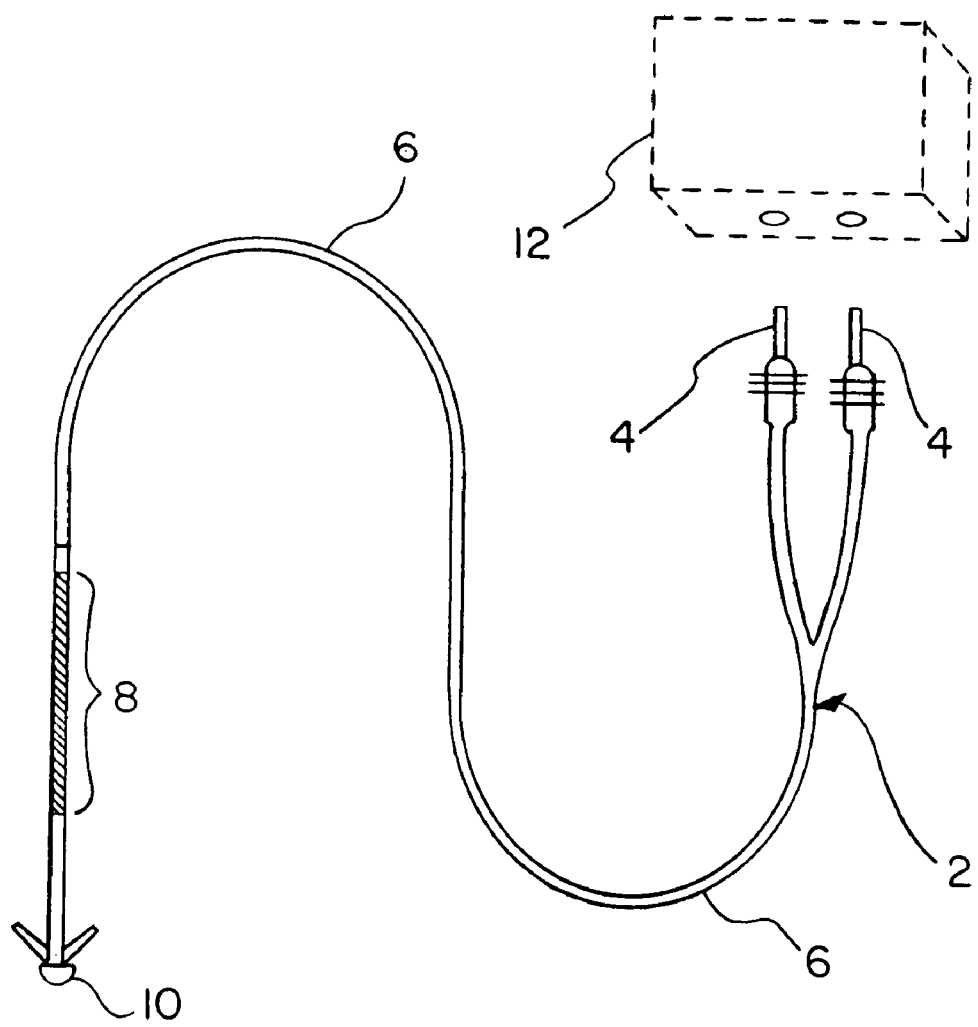
FIG. 1 is an isometric view of a typical defibrillator lead assembly.

FIG. 1 is an isometric view of a typical defibrillator lead assembly 2 of the present invention, including connectors 4, lead body 6, distal tip electrode 10, stimulator 12 and a covered, coiled electrode portion 8. The implantable lead assembly 2 and the stimulator 12 comprise a defibrillation system.

Figure 2:
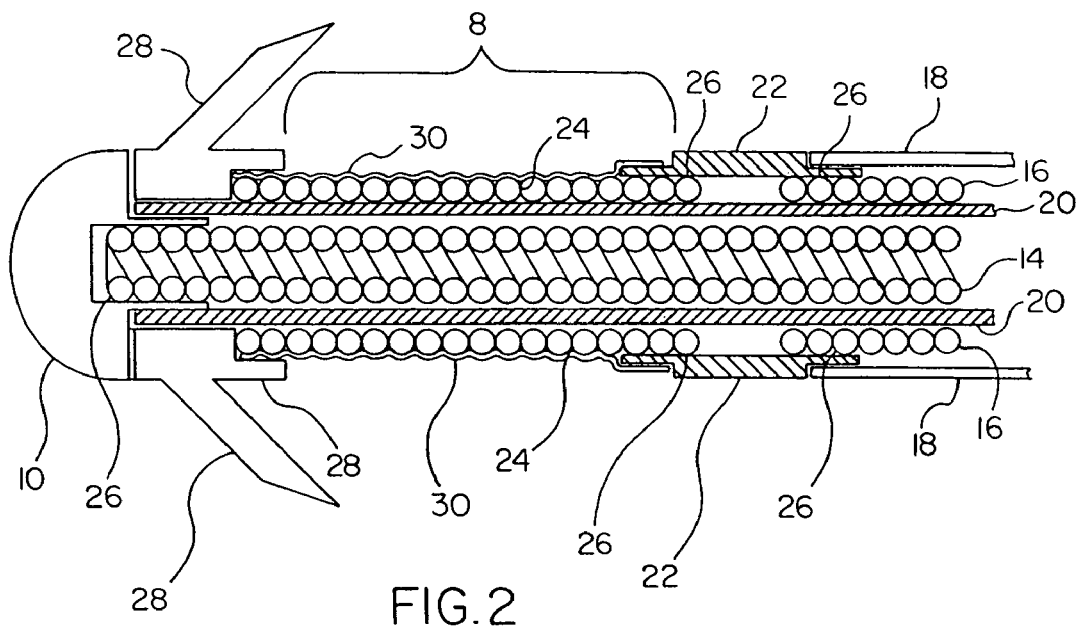
FIG. 2 is a cross-sectional view of a distal tip of a typical implantable defibrillator lead.

FIG. 2 is a cross-sectional view of a distal tip of an implantable defibrillator lead. A coiled electrical conductor 14, is attached to a distal tip electrode 10 by crimping or welding the tip to the conductor. Various crimp or weld positions are denoted by item 26. Typical crimp attachments often incorporate an internal tubular support or crimp ring, which are not shown for clarity. Electrical conductor 14 is co-axially covered by an insulator 20. A second electrical conductor 16, is co-axially covered by a lead body insulator 18. This second electrical conductor 16, is attached to an electrode connector 22. A coiled electrode 24 is attached to the opposing end of the electrode connector 22. The coiled electrode 24, which is exposed to bodily fluids, is typically fabricated from a non-corrosive, bio-compatible metal such as platinum, titanium or alloys such as platinum/iridium. A porous thin film 30, is shown covering the coiled electrode 24 and partially covering an electrode connector 22. The opposing ends of the coiled electrode 24 and film covering 30 are secured by a molded tine component 28. Other configurations can be utilized to secure the opposed end of the electrode cover. For example, the free end of the film cover could be secured by a portion of the lead body.

Figure 3:
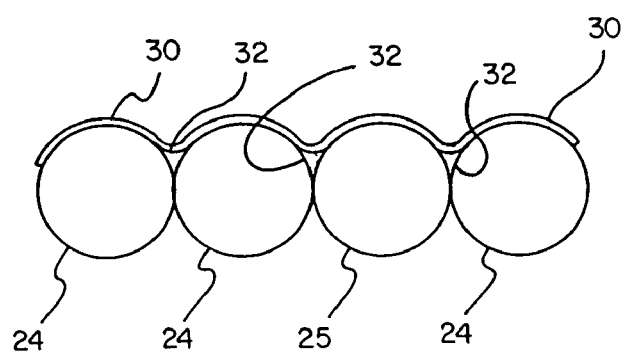
FIG. 3 is an enlarged partial cross-sectional view of a coiled electrode, showing the tightly conforming and thin film covering of the present invention.

FIG. 3 describes an enlarged partial cross-sectional view of a coiled electrode 24, showing the tightly conforming and thin film covering 30. As shown in FIG. 3, the film is drawn into the gaps 32 between the individual electrode sections 24, thereby eliminating or substantially reducing the air volume in the gaps 32. The covering of the present invention tightly conforms to the coiled electrode as a result of the process used to apply the film. This application process allows a covering to be applied and subsequently contracted tightly onto the profile of the electrode, resulting in a tightly conforming cover. A "tightly conforming cover" can be defined as a cover having a zero clearance, i.e., in physical contact with, at least a portion of the mating coiled electrode.

In a preferred embodiment, the porous thin film covering is formed from expanded polytetrafluoroethylene (ePTFE) having a specific microstructure designed to inhibit cellular penetration and ingrowth. Tissue ingrowth into the outer surface of an implanted electrode undesirably anchors the device in the tissue, thereby increasing the difficulty of explanting the electrode. An implanted device having a smooth non-porous or very small-pored outer surface inhibits tissue ingrowth, resulting in very little or no tissue attachment. Such surfaces reduce the force required to extract the implanted device. Implanted surfaces having small pores typically have some small focal points of tissue attachment along with areas covered with a proteinaceous layer.

The electrode cover of the present invention made from ePTFE film has interconnected pores that define openings or paths between the outer cover surface and the inner covered electrode. The pores are sized to allow penetration of conductive bodily fluids while restricting the ingrowth of tissue. Adequately small pore sizes minimize localized attachment and cellular ingrowth.

In a preferred embodiment, the porous thin film covering is comprised of a thin, high strength, stretched, non-woven web of polytetrafluoroethylene composed substantially of nodes interconnected by fibrils, wherein the nodes are very small, thus the material is essentially node-less. This film has a mean fibril length of less than about 3.0 microns with a preferred range of less than about 1.0 microns and more preferably between about 0.05 and 0.4 microns. The thickness of the film is, in a preferred embodiment, between about 1 micron and about 25 microns. The cover is constructed with as many as 120 layers or more of this film.

The mean fibril length of ePTFE films is estimated by examination of scanning electron photomicrographs of the surfaces of the particular film samples.

The small size of the pores of the exterior surface of the cover provides a barrier to tissue attachment into the electrode. The phrase "barrier to tissue attachment" describes a covering material that limits cellular ingrowth within and between windings of electrode coils. As a result, leads are typically removable at a time after implantation with only the application of a tensile force of less than about 2.26 kg in a relatively short time (e.g., less than about 5 minutes for withdrawal). The lead removal is therefore relatively atraumatic and is considered to be easily extracted from a body within which it has been implanted. The exterior surface of the cover thus has a pore size small enough to substantially preclude cellular penetration, although it is recognized that the cover may have some larger pores that accept a minor amount of cellular ingrowth in an overall amount that does not excessively interfere with removability of the electrode.

Tissue attachment is defined as sufficient cellular penetration into the cover that results in significantly increased force to remove the device. Some attachment is acceptable. The pore size criteria is therefore very conservative since it precludes any cellular penetration. It is recognized, however, that certain areas of the cover that have large pores on the surface may exist and may not be identified by the sampling method described below. The cover may still provide an acceptable barrier to tissue attachment.

Adequately small pore size of the microstructure of the exterior surface of the electrode covering may be determined by photomicrographs of this surface made with a scanning electron microscope. Magnification should be adequate to provide a photographic image representing an area having a length of at least 60 microns and a width of at least 40 microns. A rectangular piece of paper or template representing a length of 6 microns and width of 2 microns is provided in the same scale as that of the photomicrograph. This area conservatively represents the size of a typical red blood cell (see, e.g., W. C. O. Tsang, "The Size and Shape of Human Red Blood Cells," M.S. Thesis, University of California, San Diego, La Jolla, Calif., 1975; Y. C. Fung, "Biomechanics, Mechanical Properties of Living Tissues," pp. 112–117, Second Edition, Springer-Verlag, 1993). When placed onto the surface of the photograph and moved around to compare against the area of individual void spaces, the rectangular paper cell representation may be conveniently used to determine if the surface described by the photograph contains void spaces large enough for a cell to penetrate. For evaluation of an electrode cover, three photomicrographs should be made, representing both ends and the middle of the length of the electrode, with the photomicrographs made 120 degrees of revolution apart (i.e., evenly spaced around the circumference of the cover). In order for an electrode cover to constitute a "barrier to tissue attachment," only a minor portion (about ten percent or less) of the void spaces described by the photomicrograph should appear to be large enough to accept the rectangular paper cell representation.

The lack of tissue ingrowth and attachment therefore provides a dissection plane after chronic implantation. This dissection plane allows the electrode to be easily extracted from a body within which it has been implanted.

A preferred porous thin ePTFE film for use as the electrode covering is made as generally taught by Bacino in U.S. Pat. No. 5,476,589. The film of this type used to create examples of covered leads described herein was of about 5 micron thickness, about 0.2 g/cc bulk density, has a matrix tensile strength of about 772 MPa and an an isopropyl alcohol bubble point of about 0.2 MPa.

Figure 4:
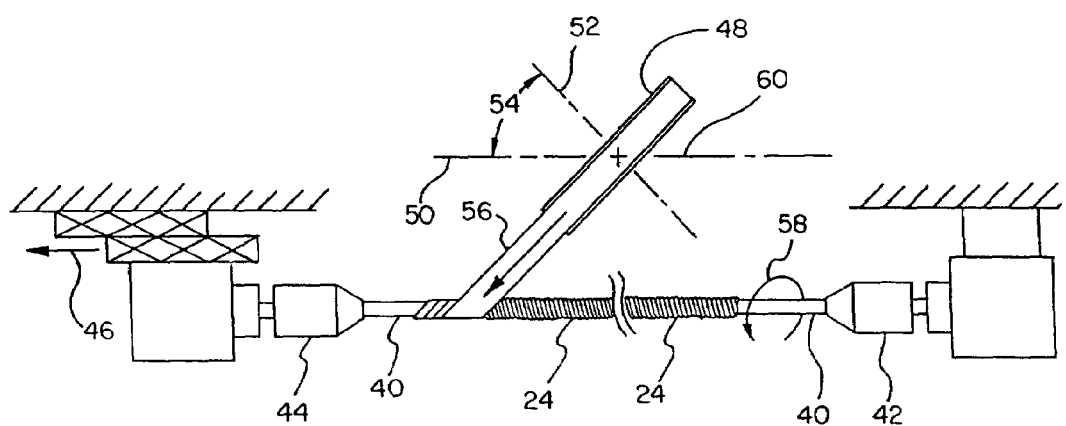
FIG. 4 is a top partial view of an automated film wrapping machine, used to apply a thin film covering onto a coiled electrode.

FIG. 4 is a top partial view of an automated film wrapping machine, used to apply the aforementioned thin film to a coiled electrode. Shown are two coiled electrodes 24, positioned onto a mandrel 40. The mandrel outer diameter is sized to provide a light frictional fit relative to the coiled electrode inner diameter. The mandrel 40, with the coiled electrodes 24, is inserted into two rotating chucks 42 and 44. The two chucks 42 and 44 are synchronously driven. Chuck 44 is adjustable parallel to the longitudinal axis of the mandrel 40 and is used to apply tension 46 to the mandrel. A spool 48, of previously described film, is positioned with the spool axis of rotation angled relative to the longitudinal axis of the mandrel. A line parallel to the longitudinal axis of the mandrel is depicted as item 50, the spool axis of rotation is depicted as item 52 and the relative angle is shown as item 54. Shown is a positive relative angle 54 of approximately 45 degrees. To initiate the wrapping process, the film 56 is hand wrapped about the mandrel, adjacent to an end of a coiled electrode. The mandrel is then rotated in direction 58 as the film spool is synchronously driven along axis 60. The film spool rotation is therefore driven by the mandrel. The film spool is magnetically braked to prevent "free-wheeling" and to control the film tension. The film spool traverses past the coiled electrodes, wrapping film onto an exposed portion of the mandrel, completing one pass. The film spool angle is then reversed and an additional film layer is applied in a helical fashion onto the previous layer as the spool travels in the opposite direction. Multiple passes can then be used to apply the desired amount of film. If the film has a higher strength in a particular direction, then the higher strength direction of the film may be oriented as desired to take best advantage of that property. Typically, for ePTFE films, the higher strength direction is the same direction as the predominant directional orientation of the fibrils.

Figure 5:
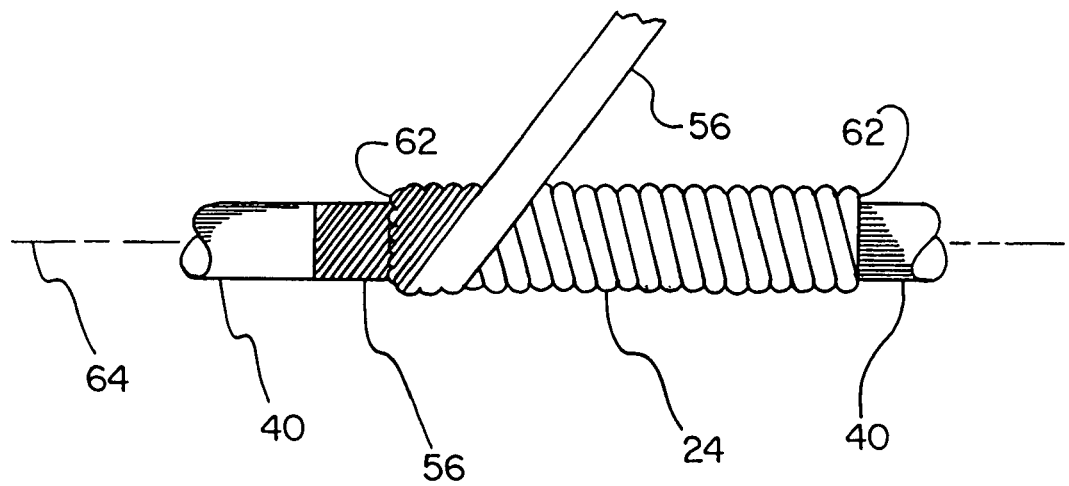
FIG. 5 is an isometric partial view of a mandrel, a coiled electrode and a partially applied film covering.

FIG. 5 is an isometric partial view of a mandrel 40, coiled electrode 24 and partially applied film 56. As shown, the film 56 is applied to the mandrel and covers the end 62, of the coiled electrode. By applying the film onto the mandrel and over both ends of the electrode, the film is effectively constrained along the longitudinal axis 64 during subsequent heat treating operations. Alternate methods for preventing longitudinal contraction include wire-wrapping, clamping or otherwise constraining the film ends prior to heat treating.

The film thickness, film width, film pitch, film spool angle and the number of passes can be tailored to achieve a desired film covering, suited for a particular electrode and application. For a typical implantable coiled defibrillation electrode, having an outer diameter of about 1.7 mm, an effective helical film wrapping is applied in six passes, using a film spool angle of 38 degrees, a film width of about 12.7 mm, a pitch of 4.2 mm traversed per mandrel revolution and an approximate film tension of about 20 to 30 grams.

Figure 6:
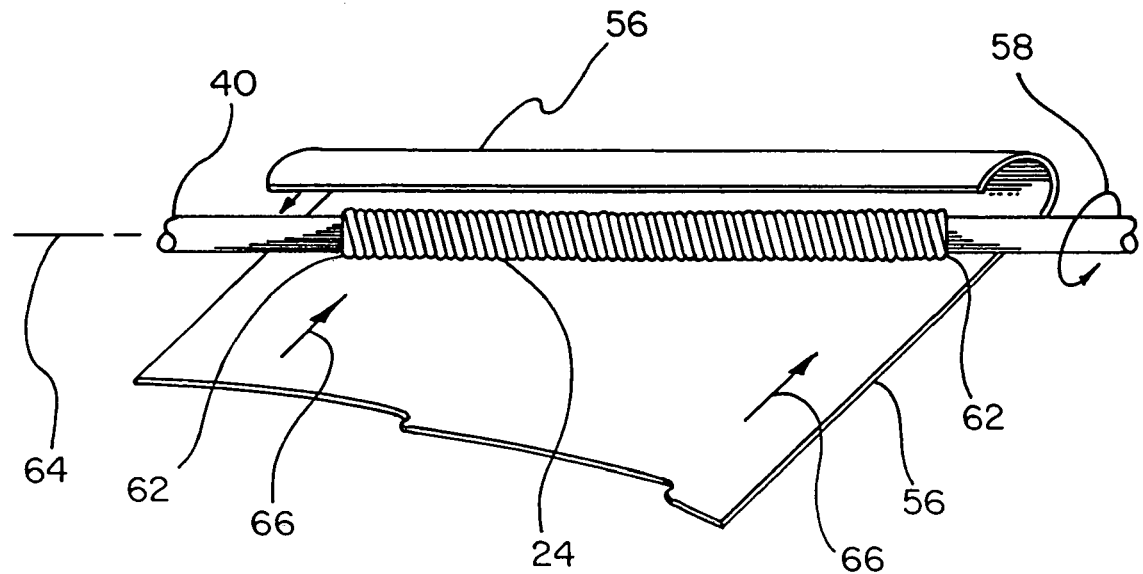
FIG. 6 is an isometric view of an alternate "cigarette" wrap used to apply a film onto a coiled electrode.

In addition to helical film wrapping, an alternate "cigarette" wrap may be employed. As shown in FIG. 6, a film 56, having a width greater than the length of the coiled electrode 24, is rolled onto an electrode in a cigarette fashion. The coiled electrode 24, is positioned onto a mandrel 40 as previously described. The mandrel and coiled electrode are rotated, for example in the direction depicted by item 58, causing the film 56 to be pulled 66 and rolled onto the electrode. As previously described in FIG. 5, the film width is sufficient to cover the ends 62 of the coiled electrode and a portion of the exposed mandrel. By applying the film onto the mandrel and over both ends of the electrode, the film is effectively constrained along the longitudinal axis 64 during subsequent heat treating operations. For a coiled electrode having an outer diameter of about 1.7 mm, and a length of 66 mm, an effective cigarette film wrapping is applied using a film width of about 86 mm, wrapping approximately 20 revolutions (20 layers of film) with an approximate film tension of about 20 to 30 grams. The higher strength direction of the film may be oriented as desired to take best advantage of that property.

To complete the film wrapping process, the film is cut from the film spool and the residual portion of film is hand positioned onto the covered electrode. The mandrel and wrapped electrode are then placed into a convection oven set at approximately 370° C. for approximately 10 minutes. The thermal process sinters the ePTFE film, adheres the film layers together and contracts the film down tightly onto the coiled electrode. As a result of this contraction, the covering tightly conforms to the coiled electrode. The covered electrode is then cooled and removed from the mandrel. Excess film edges are then trimmed and the covered electrode assembly is then staged for a subsequent chemical treatment.

The film-covered electrode is then chemically treated to decrease the time required for wetting of the film when exposed to bodily fluids. Rapid wetting of the film enhances the electrical conduction through the porous film covering soon after implantation.

In the first step of a preferred chemical treatment to increase the rate of film wetting, a film covered electrode assembly as previously described, is soaked in isopropyl alcohol (IPA) at ambient temperature (approximately 23° C.) for approximately 15 minutes. The electrode assembly should be rapidly transferred between subsequent processing steps to prevent de-wetting or drying out of the assembly.

Secondly, the covered electrode assembly is transferred from the IPA into a solution of approximately 2% polyvinyl alcohol (PVA) and de-ionized water. The solution is at ambient temperature and stirred continuously. The covered electrode assembly is soaked for about 70 minutes, after which the electrode assembly is rinsed in ambient temperature de-ionized water for about 20 minutes.

Next, the rinsed electrode assembly is soaked in an approximate solution of 2% gluteraldehyde, 1% hydrochloric acid (HCL) and de-ionized water for about 50 minutes. This solution is also at ambient temperature and stirred continuously. Following removal from this solution, the electrode assembly is rinsed in ambient temperature de-ionized water for about 2 hours, and then allowed to dry in ambient air.

The covered, PVA treated electrode is then incorporated into a typical lead assembly. The treated cover is essentially non-conductive in a dry state. Such PVA treated covered electrodes have an electrical resistance of at least 100 ohms when dry or not wetted. An electrode cover that is "non-conductive in a dry state" is hereby defined as a cover that has an electrical resistance of at least about 100 ohms when measured in a dry state.

The film wrapping and chemical treatment process described above can be applied to a variety of lead or component configurations. For example, the lead of FIG. 1 may have more than one electrode portion 8. The separate electrode sections can be individually wrapped, heat-treated, PVA treated and then incorporated into the lead final assembly. The wrapping and PVA treatments, as described above, may be utilized on a coiled electrode that has been pre-crimped or welded to an adjoining component. For example, as shown in FIG. 2, the coiled electrode 24 can be attached to an electrode connector 22, prior to film wrapping. A lead assembly, prior to the molding of the tines 28, can be processed as described above to cover the exposed portion of an electrode. In addition, the film wrapping techniques described above can be combined or modified. For example, a number of film layers can be applied in a helical fashion with other film layers utilizing a "cigarette" technique. The film can also be varied. For example, films of the same or different materials, or films with different physical characteristics, can be combined during the wrapping process.

Figure 7A:
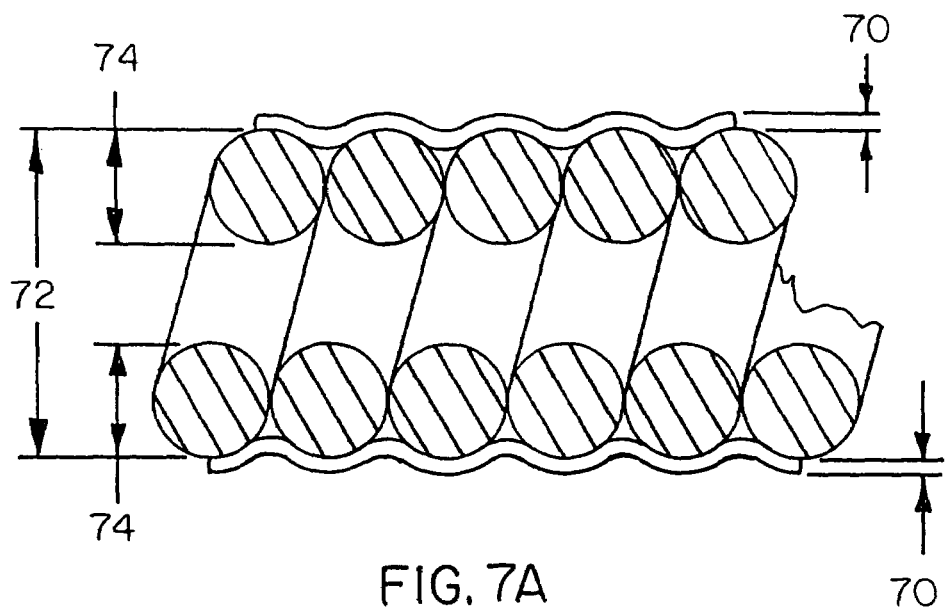
FIGS. 7A and 7B are partial cross-sectional views of a coiled electrode having a thin covering of the present invention.
Figure 7B:
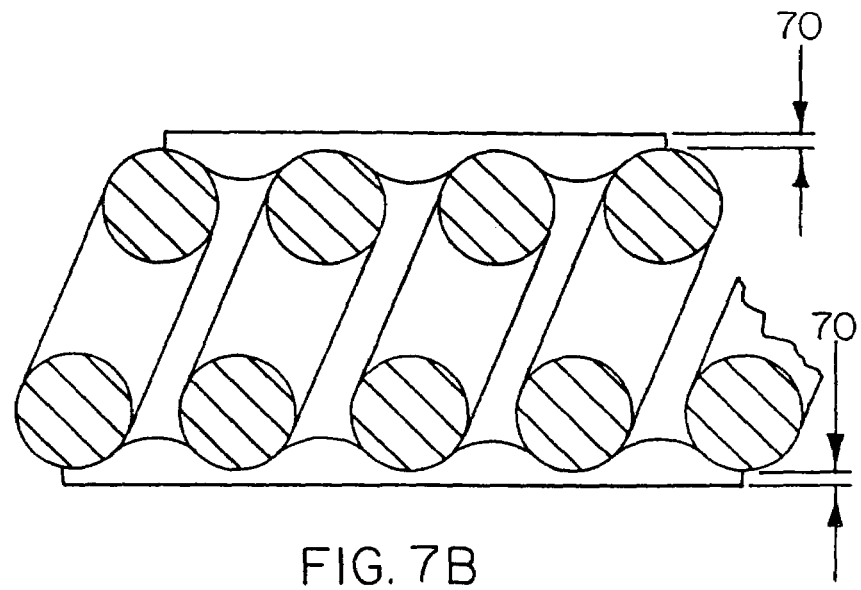

As shown in FIGS. 7A and 7B, the film or electrode cover thickness 70 is substantially less than a coiled electrode diameter 72 or a conductor wire diameter 74. The relative difference between a cover thickness and a coiled electrode diameter can be expressed as a ratio of coiled electrode diameter divided by a cover thickness. For a typical coiled electrode diameter of about 1.8 mm and a cover thickness of about 0.05 mm, this ratio is about 35:1. For an alternative coiled electrode of 1.3 mm diameter having a cover of 0.13 mm thickness, the ratio is 10:1. The thin cover of the present invention, can have ratios of coiled electrode diameter divided by cover thickness of greater than about 10:1, 20:1, 30:1, 35:1, 40:1, 50:1, 75:1 and 100:1. Cover thickness 70 of the present invention can be about 0.25 mm or less, about 0.23 mm or less, about 0.20 mm or less, about 0.18 mm or less, about 0.15 mm or less, about 0.13 mm or less, about 0.10 mm or less, about 0.07 mm or less, about 0.06 mm or less, about 0.05 mm or less, about 0.04 mm or less, about 0.03 mm or less, about 0.02 mm or less, about 0.01 mm or less. Cover thickness can be determined by measurement of a transverse cross-section of a covered electrode using an optical comparator, or other suitable means.

Figure 8A:
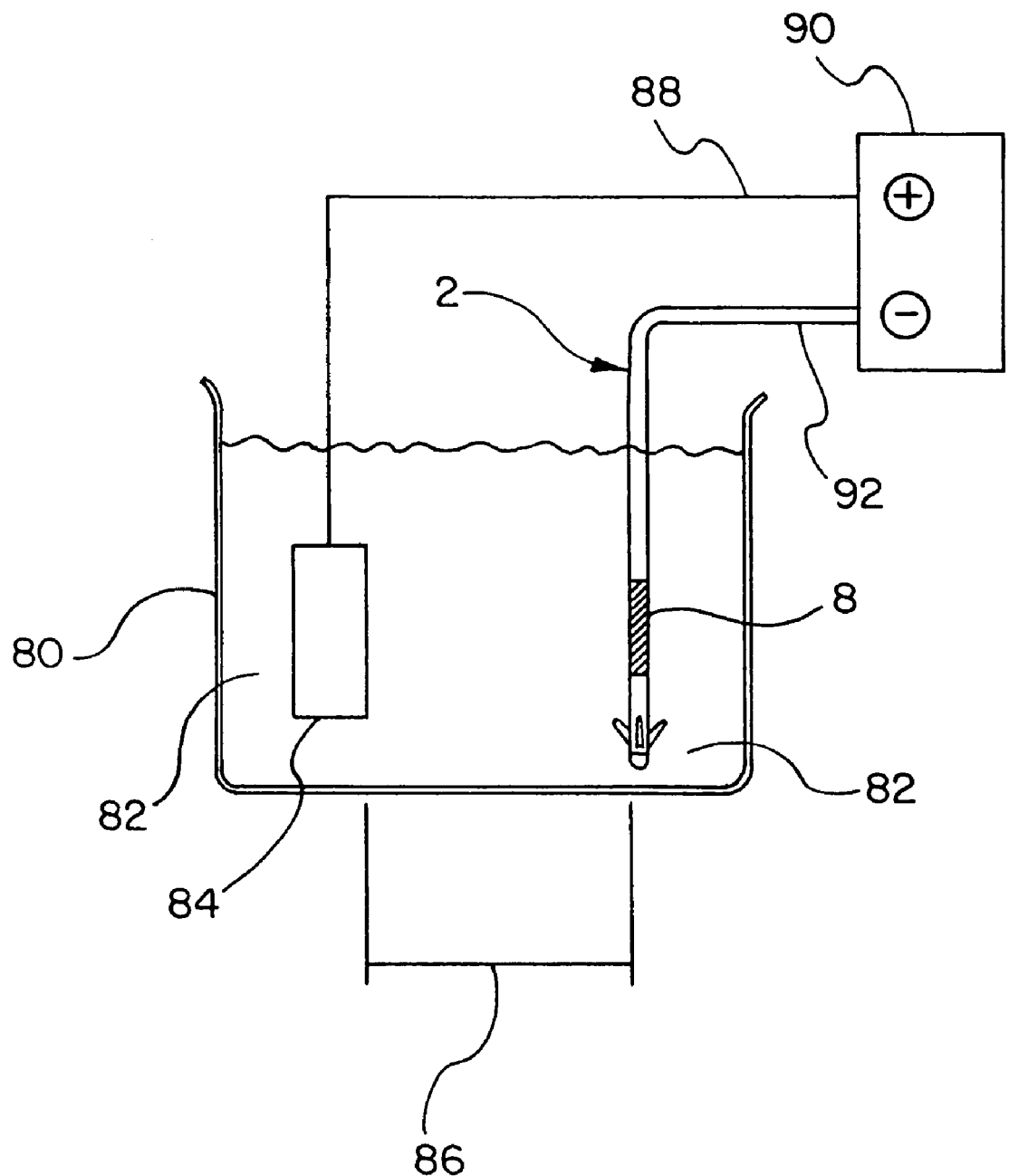
FIG. 8A is a test schematic used to demonstrate the transmission of repeated, high-energy electrical discharges through the cover of the present invention.
Figure 8B:
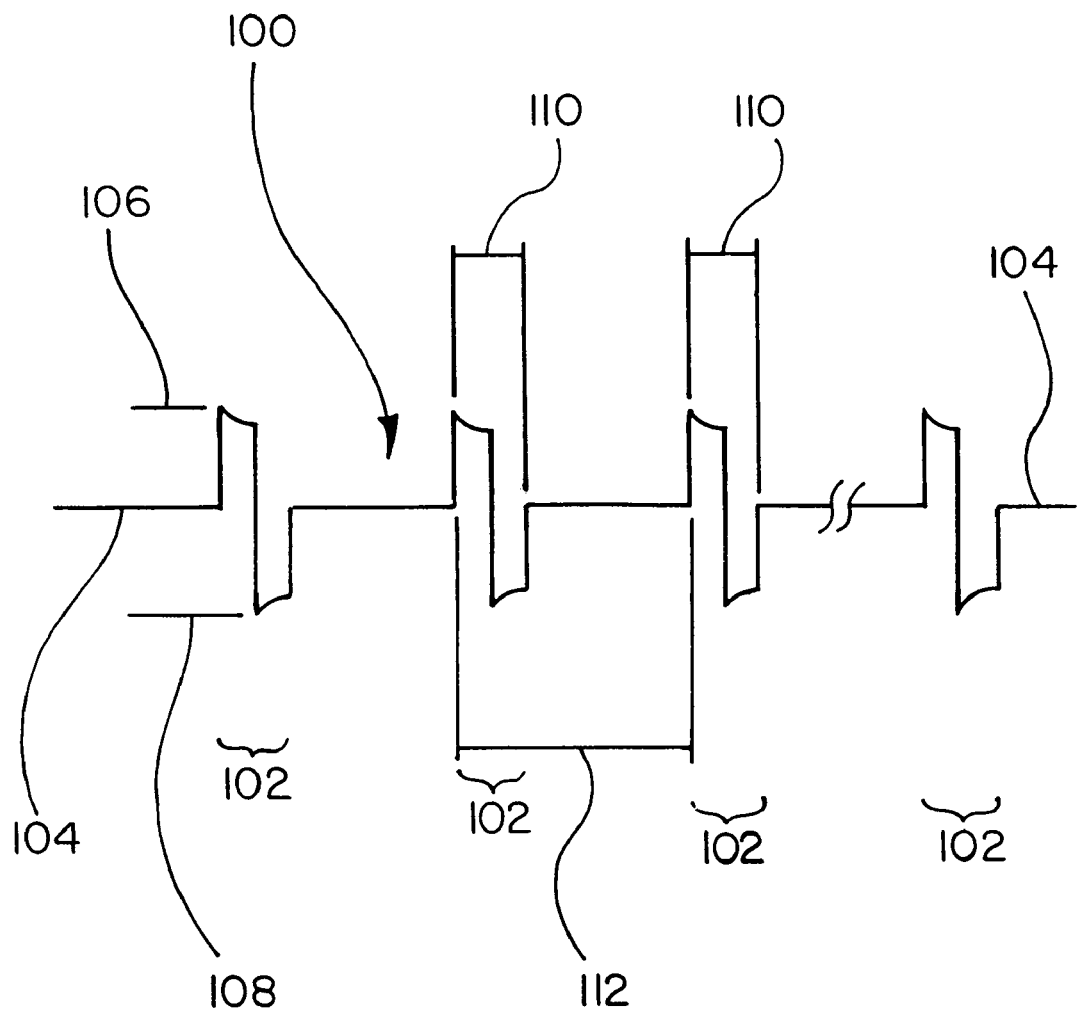
FIG. 8B is a voltage vs. time waveform, used to discharge a series of electrical pulses through a covered electrode of the present invention.

The covering of the present invention can rapidly re-wet and transmit repeated, high-energy electrical discharges without significant effect due to electrode bubble formation or mechanical disruption of the cover, as demonstrated by the following test. FIG. 8A shows a glass beaker 80, containing a solution 82 of 0.45% sodium chloride (NaCl). A lead 2, having a covered, coiled electrode portion 8, is submerged into the solution 82. An indifferent electrode 84 is separated from the covered electrode 8, by a minimal distance 86 of about 50 mm. The indifferent electrode 84, is connected to the positive connection 88 of a pulse generator 90 (Ventritex HVS-02 Cardiac Electrophysiology Device, Model HV-0200, Sunnyvale, Calif.). After the electrode portion 8 has been submerged in the saline solution for one minute, the covered electrode 8 is connected to the negative connection 92, of the pulse generator. With the pulse generator set to an amplitude of 730 volts, a series of biphasic single cycle electrical pulses, described by the plot 100 of voltage versus time shown in FIG. 8B, are then transferred between the covered electrode portion 8 and the indifferent electrode 84. The voltage is applied in a series of similar pulses 102 about a zero voltage reference 104. The time duration 110, of a typical pulse 102, is about 10 milliseconds and the time duration between pulses 112 is about 10 seconds. A series of about 200 pulses 102 are delivered to the covered electrode under test. During each electrical pulse 102, the system impedance is measured so that the total change in impedance throughout the test duration is quantified. An absence of sparks is visually confirmed during the test. Upon completion of the test, the covered electrode is examined under 30x magnification for mechanical disruption such as electrode cover burn through or holes. The lack of visually apparent mechanical disruption of the cover is evidence of the ability of the cover to rapidly re-wet during the transmission of the series of electrical pulses. Without the ability to rapidly re-wet, mechanical disruption of the cover can be expected to occur. This test thus demonstrates the adequacy of wetting initially and between cycles. Passing the test is indicative of the ability of the lead to deliver sufficiently high power and that the electrode cover does not suffer mechanical damage from the electrical challenge.

In a preferred, abbreviated version of the above-described test, only 20 pulses are used, separated by an interval of 30 seconds. When tested with 20 pulses, leads of the present invention indicated impedances of about 50 ohms to about 80 ohms. The cover thickness, cover pore size, wetting agents, and tight conformance to the electrode, allow the electrode covering of the present invention to rapidly re-wet after each electrical discharge. This rapid re-wetting enhances gas dissolution into the surrounding fluid environment and prevents sparks and degradation of the electrode cover. An electrode cover which provides "effective conduction of a defibrillation electrical charge" is hereby defined as an electrode cover which exhibits no visually apparent mechanical disruption (when viewed with 30x microscopy) after tested in accordance with the 20 pulse test method described above. In vivo testing of leads of the present invention confirmed their effectiveness, consistent with the results of the electrical pulse tests.

A covered electrode assembly that is "non-conductive in a dry state" will exhibit at least about 100 ohms of resistance and preferably more than about 500 ohms of resistance when subjected to the following test:
1) The electrode is allowed to air dry in an open environment for seven days at room temperature (21° C., +/−3 degrees) with an ambient humidity of less than 30%.
2) After the completion of the drying process, a suitable ohm/voltage meter, such as a Hewlett Packard Multimeter Model 34401A is used to measure the resistance between the lead connected to the electrode and the surface of the electrode cover.
3) The test is invalid if the electrode cover is severely compressed, damaged or penetrated by the ohmmeter probe. To prevent such compromise of the electrode cover, the multimeter test probe used to contact the electrode cover is connected to a copper shim. The shim is approximately 0.5 mm thick, approximately 5 mm wide and approximately 30 mm long with smooth burr-free edges. The 5 mm width of the shim is placed into contact with the electrode cover and a light force of approximately 50 grams is applied during the electrical measurement.

Figure 9:
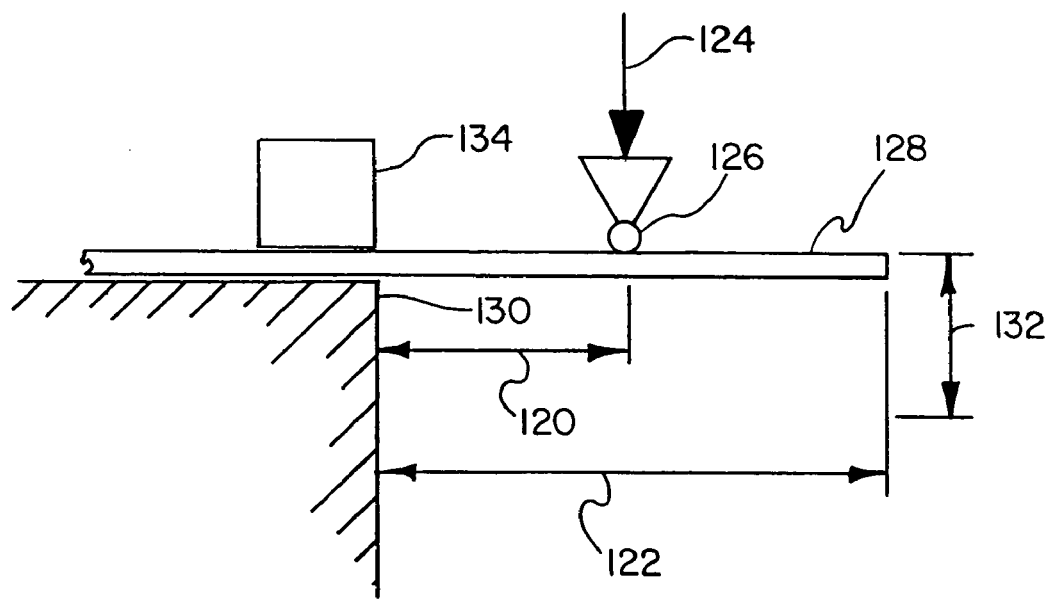
FIG. 9 is a partial side view of the force to deflect, or stiffness test, used to evaluate covered electrodes of the present invention.

The force to deflect test indicative of flexibility is depicted in FIG. 9. Flexibility is an important feature of defibrillator electrodes. All examples of covered electrodes demonstrate good flexibillity when compared to uncovered leads. FIG. 9 shows an electrode under test 128, a cantilever support 130 and a load fixture 126. Using a suitable load vs. displacement instrument, such as an Instron model 5564 (Instron Corporation, Canton, Mass.), a load 124 is applied to the electrode under test 126. The load 124 is applied to the electrode at a length 120, which is one half of the total overhung length 122. For example, for a total overhanging length 122 of 2 cm, the load application length 120 is one cm. The load 124 is applied at a 20 mm per minute descent rate. The electrode 128 is constrained to the cantilever support 130 by a weight or clamp 134. The load 124 is applied until the electrode under test is deflected, at the loading point, by a length 132. The deflection length 132 is equal to the load application length 120. The test is performed at ambient temperature (26° C.). An applied load vs. deflection plot is first generated for a covered electrode. The cover is then removed by laser trimming or other suitable means and the bare electrode is re-tested. The applied load vs. deflection plots for the covered vs. uncovered electrode are then compared to determine the additional stiffness accredited to the cover.

Figure 10:
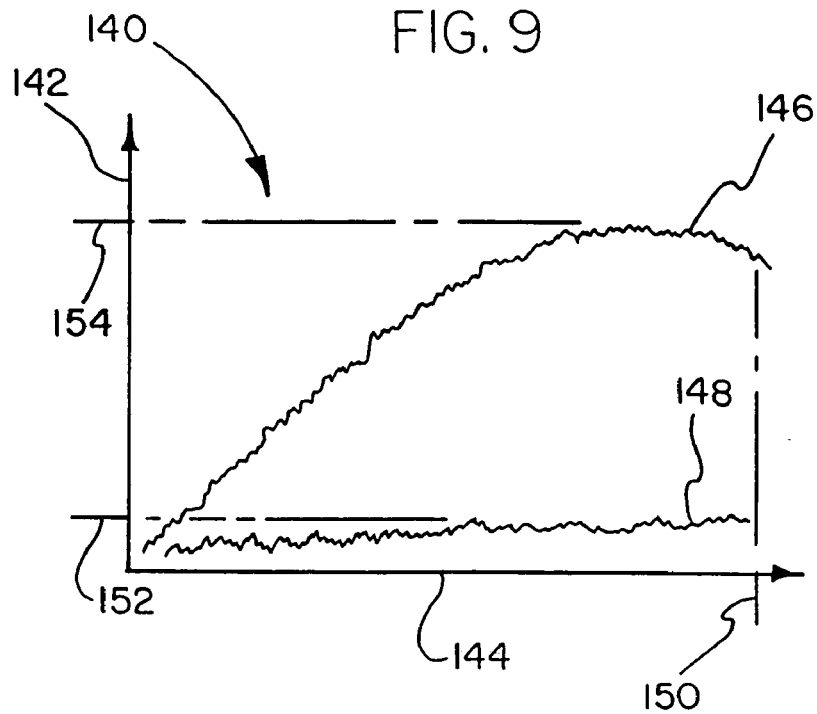
FIG. 10 displays a force vs. displacement plot of typical covered and uncovered electrodes. Such plots quantify the relative stiffness accredited to the electrode cover of the present invention.

A typical applied load vs. deflection plot, generated during this test, is depicted in FIG. 10. Shown is a load vs. deflection plot 140, for a covered electrode 146, and an uncovered electrode 148. The vertical axis 142 reflects the applied load while the horizontal axis 144 reflects the displacement. The maximum displacement 150 relates to the load application length 120 as previously described. The maximum applied load 154 for the covered electrode is graphically or digitally determined. Similarly, the maximum applied load 152 for the uncovered electrode is determined. The maximum applied load 154 for the covered electrode is then divided by the maximum applied load 152 for the uncovered electrode. This result is a ratio of covered electrode stiffness to uncovered electrode stiffness. Covered electrodes with the lowest ratio values are thus the most flexible and most preferred. Electrode covers of the present invention have ratios of covered electrode stiffness to uncovered electrode stiffness of less than about 100:1, less than about 75:1, less than about 50:1, less than about 35:1, less than about 30:1, less than about 25:1, less than about 20:1, less than about 15:1, less than about 10:1, less than about 5:1, less than about 3:1, less than about 2:1 and less than about 1.5:1.

The durability of covered electrodes of the present invention was evaluated on a high-rate oscillatory fatigue tester. After repeated fatigue cycles, the electrode lead cover is visually examined for any de-lamination, splits, rips or any other visual differences or changes. Typical covered electrodes of the present invention have been subjected to over 475,000,000 cycles without any visual degradation.

Figure 11A:
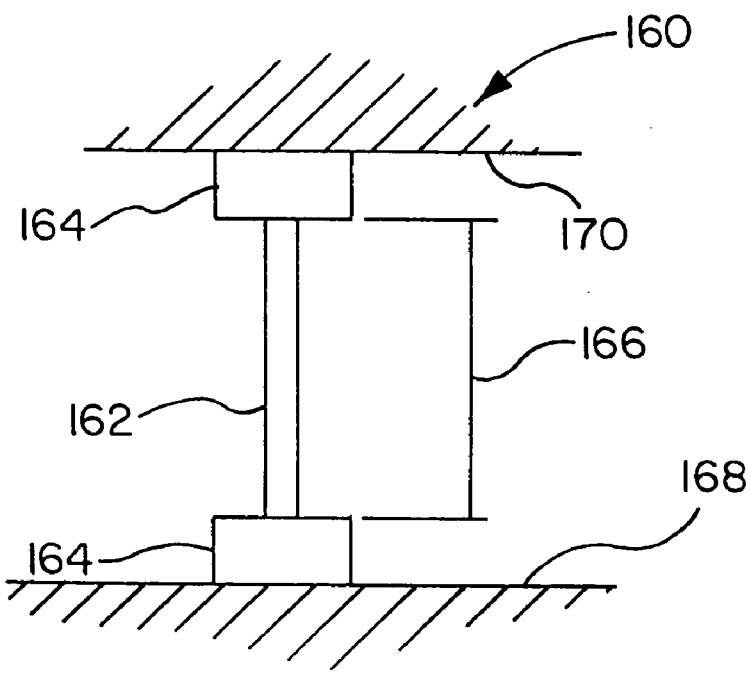
FIGS. 11A and B show a partial side view of the high rate flex tester used to evaluate the fatigue life of covered electrodes of the present invention.
Figure 11B:
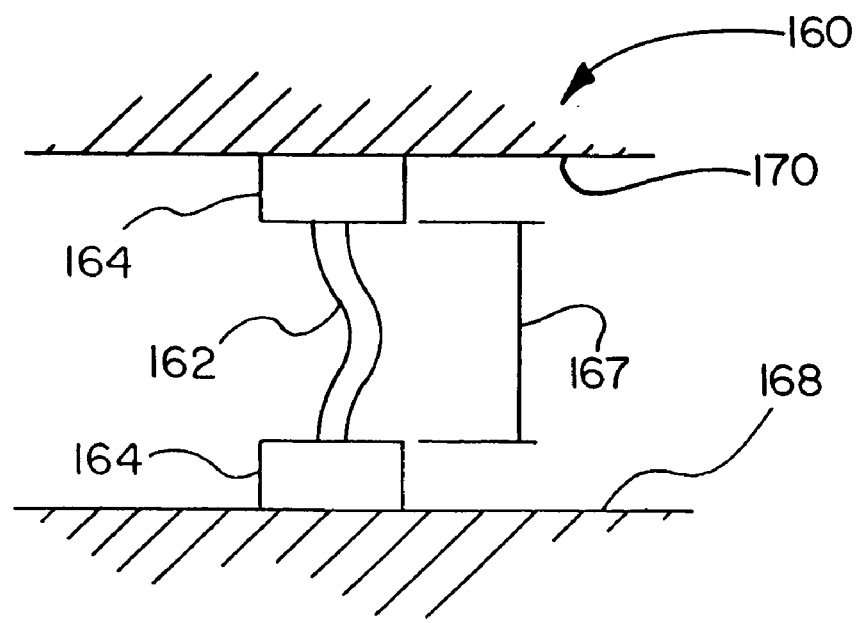

The fatigue life test is depicted in FIGS. 11A and B. Shown is a partial side view of the high rate flex tester 160, covered electrode mounting fixtures 164, and a covered electrode under test 162. The upper mounting surface 170 is driven by a high rate displacement solenoid (not shown) and is displaced relative to the stationary lower mounting surface 168, causing the electrode to bend as shown in FIG. 11B. The electrode under test is initially mounted to have an un-tensioned length 166. The displacement of the oscillating surface 170 is adjusted to the dimension 167, which causes the electrode to cyclically deform during the test. The upper surface 170 oscillates at a 30 Hz rate, the initial un-tensioned length 166 is 32 mm±0.3 mm and the displacement of the upper surface 170 is 1.3 mm±0.13 mm resulting in a length 167 of 31 mm.

Figure 12:
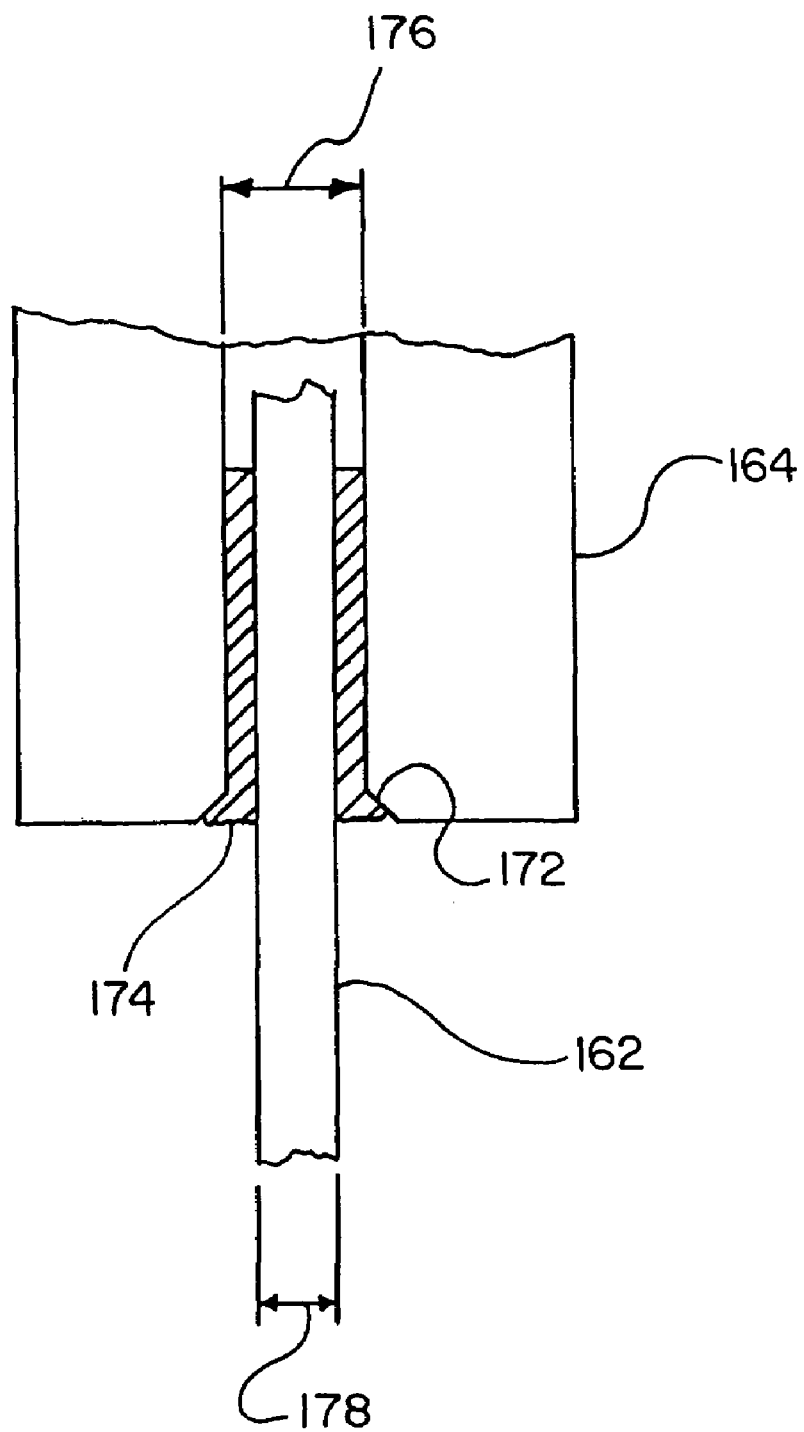
FIG. 12 is a partial cross-sectional view of a fixture used to mount covered electrodes of the present invention onto the high rate flex tester.

Details relating to the mounting fixture 164, are depicted in FIG. 12. Shown is a partial cross-sectional view of a mounting fixture 164 and a electrode 162. The mounting fixture hole has a diameter 176 that is typically sized to be approximately 20% larger than the electrode diameter 178. The electrode is secured to the mounting fixture by a silicone adhesive 174 and is applied to fill the chamfer 172 on the mounting fixture. The electrode can be prepared for the high rate fatigue test by securing two mounting fixtures 164, at the required separation and then curing the adhesive. In an alternate method, one end of the electrode can be bonded to a mounting fixture and placed onto the tester. The other electrode end can then be bonded to its mounting fixture in place after the separation distance is set on the tester.

Typical covered electrodes of the present invention have been subjected to over 1,000,000 cycles, over 5,000,000 cycles, over 10,000,000 cycles, over 25,000,000 cycles, over 100,000 cycles, over 100,000,000 cycles, over 200,000,000 cycles, over 300,000,000 cycles and over 475,000,000 cycles of the previously described test, without any visual degradation of the cover. This testing indicates that the leads of the present invention can provide good durability.

Figure 13A:
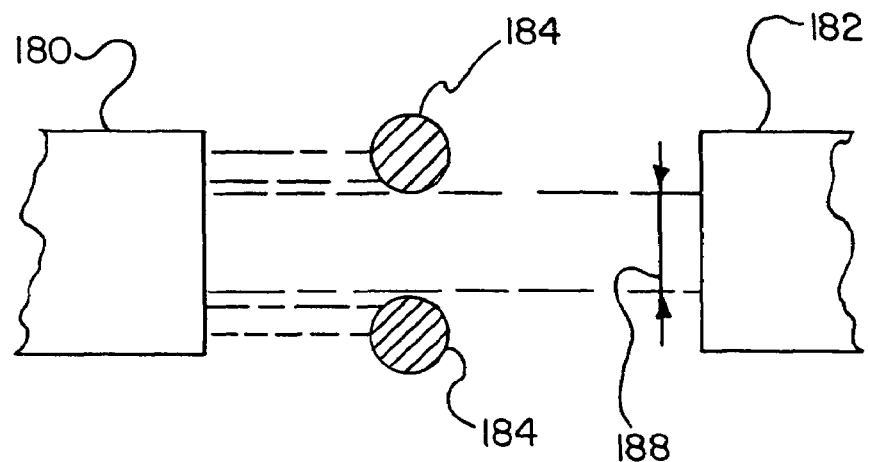
FIGS. 13A and B are partial side views of a laser micrometer used to measure the thickness of thin films used in the manufacture of electrode coverings.
Figure 13B:
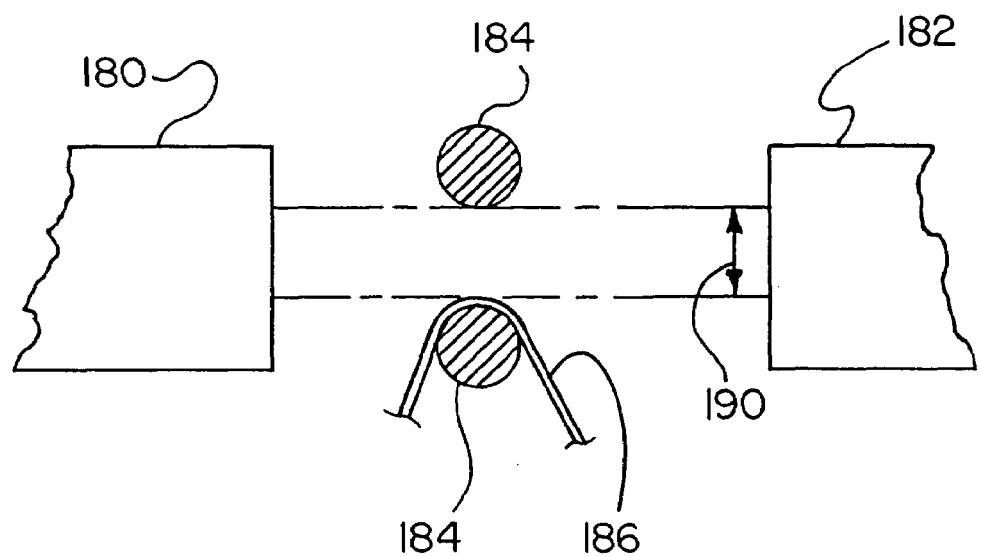

The thickness of each of these samples was measured using a laser micrometer (Keyence model no. LS-3100). As shown in FIGS. 13A and B, two metal gage pins 184 were aligned between a laser micrometer source 180 and a laser micrometer receiver 182. The separation or gap 188 between the pins is transposed onto the receiver 182. This indicated distance 188 was then reset as the "zero" reading of the laser micrometer. As shown in FIG. 13B, a single layer of film 186 is draped over the surface of one of the metal pins 184 without overlap and without wrinkles. The laser micrometer then indicated the resulting dimension 190 as the thickness of the film sample.

Sample weights were determined using a Mettler model no. PM400 analytical balance (Mettler Instrument Corporation, Hightstown, N.J.). The density was then calculated as the sample weight divided by the bulk sample volume.

The film used was of about 5 micron thickness, about 25.4 mm width and 91.4 cm length, and had a density of about 0.2 g/cc.

The electrode cover adds strength which aids in device removal. The cover can be altered to increase this effect (by the use of different wrap orientations, differing amounts of wrap, the use of different types of film, etc.). Strength of the ePTFE covering material is indicated by matrix tensile strength. Because the ePTFE films used to make the electrode covers are porous materials, tensile strength values were converted to matrix tensile strength values in order to compensate for differing degrees of porosity. Matrix tensile strength was obtained by multiplying the tensile strength of each individual sample by the ratio of the 2.2 g/cc density of solid, non-porous PTFE to the density of the porous sample. Test sample density was determined as its mass divided by its bulk volume (gross length times gross width times gross thickness).

Tensile testing was carried out on an Instron Tensile Testing Machine, model no. 1122 (Instron Corporation, Canton, Mass.). Testing was performed according to Test Method A of ASTM Standard D882–91. All samples were cut to a length of 45.7 cm and a width of 2.54 cm. The thickness of each cut sample was determined by the above-described laser micrometer measurement procedure. The gauge length after allowing for sample grip length was 100 mm; Instron pneumatic grips were used for all testing at an operating pressure of 0.6 MPa. Rubber-coated grip faces were used in order to prevent grip breaks in this material. Testing was performed at a rate of 50 mm/min resulting in a strain rate of 50%/min. From the resulting plot of force vs. displacement provided by the testing machine and from measurements of sample thickness, width and gauge length, values were determined for tensile strength.

EXAMPLES

The following is a description of the manufacture and evaluation of various electrodes of the present invention. To evaluate alternate configurations of covered electrodes, examples were fabricated using two different film types, three different film wrapping orientations, various cover thicknesses and two different coil diameters. Table 1 summarizes the manufacturing parameters while Table 2 summarizes evaluation parameters.

Example 1

Titanium wire, approximately 0.2 mm in diameter, was wound in a quad-filar coil having an outer diameter of approximately 2.4 mm. The film used to form the electrode cover was a thin, high strength, stretched, non-woven web of polytetrafluoroethylene composed substantially of nodes interconnected by fibrils, wherein the nodes were very small, thus the material was essentially node-less. This film had a mean fibril length of less than about 1.0 microns. The film was made as generally taught by Bacino in U.S. Pat. No. 5,476,589. The film of this type had a thickness of about 4.8 microns, a bulk density of about 0.2 g/cc, a matrix tensile strength of about 772 MPa in the higher strength direction and an isopropyl alcohol bubble point of about 0.2 MPa. This film is referred to as "Film Type A" in Tables 1 and 2. Twenty layers of this film were applied to the coil using the helical wrapping and heat treating process previously described. The resulting electrode cover was approximately 0.019 mm thick. The electrode cover was then chemically treated with PVA as previously described.

Example 2

An alternate covered electrode was produced in accordance with Example 1, except 20 layers of film were applied in a cigarette configuration as previously described. The higher strength direction of the film was oriented to be substantially parallel to the longitudinal axis of the electrode.

Example 3

An alternate covered electrode was produced in accordance with Example 1, except 2 layers of film were applied in a cigarette configuration as previously described. The higher strength direction of the film was oriented essentially 90 degrees relative to the longitudinal axis of the electrode.

Example 4

An alternate covered electrode was produced in accordance with Example 3, using an expanded PTFE film, having a thickness of 0.09 mm, a Gurley number of 39.5 seconds and an isopropyl alcohol bubble point of 0.334 MPa. This film had an essentially balanced or bi-directional strength, so the higher strength direction relative to the longitudinal axis of the electrode was not relevant. This film is referred to as "Film Type B" in Tables 1 and 2.

Example 5

An alternate covered electrode was produced in accordance with Example 3, except 120 layers of film were applied in a cigarette configuration as previously described. The higher strength direction of the film was oriented essentially 90 degrees relative to the longitudinal axis of the electrode.

Example 6

An alternate covered electrode was produced in accordance with Example 3, except 20 layers of film were applied in a cigarette configuration as previously described. The higher strength direction of the film was oriented essentially 90 degrees relative to the longitudinal axis of the electrode.

Example 7

Titanium wire, approximately 0.2 mm in diameter, was wound in a quad-filar coil having an outer diameter of approximately 1.7 mm. Twenty layers of the film used in Example 1 were applied to this coil using the helical wrapping and heat treating process previously described. The resulting electrode cover was approximately 0.05 mm thick. The electrode cover was then chemically treated with PVA as previously described.

Example 8

An alternate covered electrode was produced in accordance with Example 7, except 20 layers of the film was applied in a cigarette configuration as previously described. The higher strength direction of the film was oriented essentially 90 degrees relative to the longitudinal axis of the electrode. The electrode cover was then chemically treated with PVA as previously described.

TABLE 1

| Example No. | Film Type | No. Film Layers | Helical Wrap | Circumferential Wrap: Higher Strength Direction | Cover Thickness | Coil Diameter |
|---|---|---|---|---|---|---|
| 1 | A | 20 | Yes | | 19.4μ | 2.4 mm |
| 2 | A | 20 | | Parallel to longitudinal electrode axis | 22.9μ | 2.4 mm |
| 3 | A | 2 | | 90° to longitudinal electrode axis | 3.7μ | 2.4 mm |
| 4 | B | 2 | | Not relevant | 79.6μ | 2.4 mm |
| 5 | A | 120 | | 90° to longitudinal electrode axis | 107μ | 2.4 mm |
| 6 | A | 20 | | 90° to longitudinal electode axis | 30.9μ | 2.4 mm |
| 7 | A | 20 | Yes | | 30.9μ | 1.7 mm |
| 8 | A | 20 | | 90° to longitudinal electrode axis | 30.9μ | 1.7 mm |

TABLE 2

| Example # | Force to Deflect Ratio Covered divided by Uncovered | Electrical Test 20 Pulse | Electrical test 200 Pulse | Fatigue Life Cycles to Date |
|---|---|---|---|---|
| 1 | 5 | Pass | Not tested | Not Tested |
| 2 | 15 | Pass | Not tested | Not Tested |
| 3 | 2 | Pass | Not tested | Not Tested |
| 4 | 35 | Pass | Not tested | Not Tested |
| 5 | 35 | Pass | Not tested | Not Tested |
| 6 | 6 | Pass | Pass | Not Tested |
| 7 | Not Tested | Pass | Not tested | >400,000,000 |
| 8 | Not Tested | Pass | Pass | >500,000,000 |

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. An implantable defibrillation lead, comprising:
   a coiled defibrillation electrode;
   a cover at least partially surrounding the coiled electrode resulting in a covered electrode;
   the cover comprising porous PTFE,
   the cover being electrically non-conductive in a dry state and conductive when implanted to provide effective conduction of a defibrillation electrical charge; and
   the cover having a thickness of less than about 0.13 mm;
   wherein the cover provides a barrier to tissue attachment.

2. The lead of claim 1 wherein the cover has a thickness of less than about 0.10 mm.

3. The lead of claim 1 wherein the cover has a thickness of less than about 0.07 mm.

4. The lead of claim 1 wherein the cover has a thickness of less than about 0.05 mm.

5. The lead of claim 1 wherein the cover has a thickness of less than about 0.04 mm.

6. The lead of claim 1 wherein the cover has a thickness of less than about 0.03 mm.

7. The lead of claim 1 wherein the cover has a thickness of less than about 0.01 mm.

8. The lead of claim 1 wherein the PTFE comprises porous expanded PTFE.

9. The lead of claim 8 wherein the ePTFE comprises multiple layers of ePTFE film.

10. The lead of claim 1 wherein when compared in a force-to-deflect test, a ratio of force-to-deflect of said covered electrode to the coiled electrode without cover is less than about 35:1.

11. The lead of claim 1 wherein when compared in a force-to-deflect test, a ratio of force-to-deflect of said covered electrode to the coiled electrode without cover is less than about 10:1.

12. The lead of claim 1 wherein said porous PTFE cover is provided with a wetting agent.

13. The lead of claim 12 wherein said wetting agent comprises polyvinyl alcohol.

14. The lead of claim 1 wherein said lead is easily extracted from a body within which it has been implanted.

15. The lead of claim 1 wherein said cover exhibits no visually apparent mechanical disruption when viewed under 30× microscopy, following testing in a saline solution with a series of 20 biphasic single cycle voltage pulses.

16. The lead of claim 1 having a fatigue life of at least 1 million cycles.

17. The lead of claim 16 having a fatigue life of at least 5 million cycles.

18. The lead of claim 16 having a fatigue life of at least 100 million cycles.

19. The lead of claim 16 having a fatigue life of at least 400 million cycles.

20. The lead of claim 1 in combination with a pulse generator.

21. An implantable defibrillation lead, comprising:
a coiled defibrillation electrode;
a cover at least partially surrounding the coiled electrode;
the cover comprising porous PTFE;
the cover being provides with a treatment of a wetting agent; and
the cover having a thickness of less than about 0.13 mm;
wherein the cover provides a barrier to tissue attachment.

22. The lead of claim 21 wherein the cover has a thickness of less than about 0.10 mm.

23. The lead of claim 21 Wherein the cover has a thickness of less than about 0.07 mm.

24. The lead of claim 21 wherein the cover has a thickness of less than about 0.05 mm.

25. The lead of claim 21 wherein the cover has a thickness of less than about 0.04 mm.

26. The lead of claim 21 wherein the cover has a thickness of less than about 0.03 mm.

27. The lead of claim 21 wherein the cover has a thickness of less than about 0.01 mm.

28. The lead of claim 22 wherein the PTFE comprises porous expanded PTFE.

29. The lead of claim 28 wherein the ePTFE comprises multiple layers of ePTFE film.

30. The lead of claim 21 wherein when compared in a force-to-deflect test, a ratio of force-to-deflect of said covered electrode to the coiled electrode without cover is less than about 35:1.

31. The lead of claim 21 wherein when compared in a force-to-deflect test, a ratio of force-to-deflect of said covered electrode to the wiled electrode without cover is less than about 10:1.

32. The lead of claim 21 wherein said wetting agent comprises polyvinyl alcohol.

33. The lead of claim 21 wherein said lead is easily extracted from a body within which it has been implanted.

34. The lead of claim 21 wherein said cover exhibits no visually apparent mechanical disruption when viewed under 30× microscopy, following testing in a saline solution with a series of 20 biphasic single cycle voltage pulses.

35. The lead of claim 21 having a fatigue life of at least 1 million cycles.

36. The lead of claim 35 having a fatigue life of at least 5 million cycles.

37. The lead of claim 35 having a fatigue life of at least 100 million cycles.

38. The lead of claim 35 having a fatigue life of at least 400 million cycles.

39. The lead of claim 21 in combination with a pulse generator.

40. An implantable defibrillation lead, comprising:
a defibrillation electrode;
a cover in contact with the electrode, said cover comprised of porous PTFE;
wherein the porous polymeric cover has a thickness of less than about 0.13 mm;
wherein the cover is non-conductive in a dry state and provides rapid re-wetting following a
transmission of a series of electrical discharges; and
wherein said lead is configured for use as an implantable defibrillator lead.

41. The lead of claim 40 wherein the cover provides a barrier to tissue attachment.

42. The lead of claim 40 wherein the PTFE comprises porous expanded PTFE.

43. The lead of claim 42 wherein the ePTFE comprises multiple layers of ePTFE film.

44. The lead of claim 40 wherein said porous PTFE cover is provided with a wetting agent.

45. The lead of claim 44 wherein said wetting agent comprises polyvinyl alcohol.

46. The lead of claim 40 wherein said lead is easily extracted from a body within which it has been implanted.

47. The lead of claim 40 in combination with a pulse generator.

* * * * *